US012262883B2

(12) United States Patent
Congdon et al.

(10) Patent No.: US 12,262,883 B2
(45) Date of Patent: *Apr. 1, 2025

(54) HEMOSTASIS CLIP WITH COLLAPSIBLE CAPSULE

(71) Applicant: BOSTON SCIENTIFIC SCIMED, INC., Maple Grove, MN (US)

(72) Inventors: Daniel Congdon, Hudson, MA (US); Laurie A. Lehtinen, Boylston, MA (US); Alex Roberts, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,296

(22) Filed: Nov. 15, 2023

(65) Prior Publication Data

US 2024/0081799 A1    Mar. 14, 2024

Related U.S. Application Data

(63) Continuation of application No. 17/645,250, filed on Dec. 20, 2021, now Pat. No. 11,849,930, which is a
(Continued)

(51) Int. Cl.
*A61B 17/00* (2006.01)
(52) U.S. Cl.
CPC .... *A61B 17/0057* (2013.01); *A61B 17/00234* (2013.01); *A61B 2017/0034* (2013.01);
(Continued)

(58) Field of Classification Search
CPC .......... A61B 17/00234; A61B 17/0057; A61B 17/1227; A61B 17/1285;
(Continued)

(56) References Cited

U.S. PATENT DOCUMENTS 3,958,576 A * 5/1976 Komiya ................. A61B 17/10
 24/537
11,849,930 B2 * 12/2023 Congdon ......... A61B 17/00234
(Continued)

FOREIGN PATENT DOCUMENTS

| CN | 101112327 | 1/2008 |
| CN | 101116606 | 2/2008 |

(Continued)

*Primary Examiner* — Mohamed G Gabr
(74) *Attorney, Agent, or Firm* — Fay Kaplun & Marcin, LLP

(57) ABSTRACT

A clipping device includes a capsule including a longitudinal body and a cap mounted over a distal end thereof so that the cap is movable relative to the longitudinal body from a pre-deployed configuration to a deployed configuration in which the cap, is moved proximally relative to the longitudinal body to reduce a length of the capsule. A channel of the cap and a channel of the capsule are substantially aligned with respect to one another. At least proximal portions of a pair of clip arms are received within the channels of the cap and the longitudinal body so that the clip arms are movable relative to the capsule between an open configuration, in which distal ends of the clip arms are separated from one another, and a closed configuration, in which the distal ends of the clip arms are drawn toward one another.

16 Claims, 4 Drawing Sheets

Related U.S. Application Data continuation of application No. 16/861,086, filed on Apr. 28, 2020, now Pat. No. 11,234,686.

(60) Provisional application No. 62/853,303, filed on May 28, 2019.

(52) U.S. Cl.
CPC ............ *A61B 2017/00584* (2013.01); *A61B 2017/00623* (2013.01)

(58) Field of Classification Search
CPC .. A61B 2017/0034; A61B 2017/00584; A61B 2017/00623; A61B 2090/037
See application file for complete search history.

(56) References Cited

U.S. PATENT DOCUMENTS

| | | | |
|---|---|---|---|
| 2018/0078262 A1* | 3/2018 | Lehtinen | ............. A61B 17/083 |
| 2018/0140300 A1 | 5/2018 | Randhawa | |
| 2019/0105046 A1 | 4/2019 | Jagelski et al. | |

FOREIGN PATENT DOCUMENTS

| | | |
|---|---|---|
| CN | 103841906 | 6/2014 |
| CN | 109640841 | 4/2019 |
| CN | 109788957 | 5/2019 |
| CN | 109803592 | 5/2019 |

* cited by examiner

HEMOSTASIS CLIP WITH COLLAPSIBLE CAPSULE

PRIORITY CLAIM

The present application is a Continuation of U.S. patent application Ser. No. 17/645,250 filed on Dec. 20, 2021, now U.S. Pat. No. 11,849,930; which is a Continuation of U.S. patent application Ser. No. 16/861,086 filed on Apr. 28, 2020, now U.S. Pat. No. 11,234,686; which claims priority to U.S. Provisional Patent Application Ser. No. 62/853,303 filed on May 28, 2019. The disclosures of the above application(s)/patent(s) are incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract, or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be required.

SUMMARY

The present disclosure relates to a clipping device, comprising a capsule including a longitudinal body and a cap mounted over a distal end thereof so that the cap is movable relative to the longitudinal body from a pre-deployed configuration to a deployed configuration in which the cap, is moved proximally relative to the longitudinal body to reduce a length of the capsule. A channel of the cap and a channel of the capsule being substantially aligned with respect to one another. The clipping device also includes a pair of clip arms, at least proximal portions of which are received within the channels of the cap and the longitudinal body so that the clip arms are movable relative to the capsule between an open configuration, in which distal ends of the clip arms are separated from one another, and a closed configuration, in which the distal end of the clip arms are drawn toward one another.

In an embodiment, a distal end of the cap may include a shoulder for abutting the distal end of the longitudinal body to prevent further proximal movement of the cap relative to the longitudinal body.

In an embodiment, the clip arms may be biased toward the open configuration so that, in the closed configuration, the clip arms drawn toward one another via contact with an interior surface of one of the cap and the longitudinal body.

In an embodiment, a proximal portion of the longitudinal body may include locking windows extending through a wall thereof.

In an embodiment, proximal ends of the clip arms may include locking tabs which are configured to engage the locking windows of the longitudinal body when the capsule is in the deployed configuration.

In an embodiment, the cap may be coupled to the longitudinal body via a shear pin configured to fail when the predetermined force is exerted thereon.

In an embodiment, the cap may be coupled to the longitudinal body via a pin extending from an interior surface thereof and through a slotted opening extending through a wall along a distal portion of the longitudinal body, the pin longitudinally slidable from a distal end of the slotted opening, in the pre-deployed configuration, to a proximal end of the slotted opening, in the deployed configuration.

In an embodiment, the distal end of the slotted opening may be sized and shaped to correspond to a size and shape of the pin, the distal and proximal ends of the slotted opening connected via a middle portion having a width smaller than the distal end of the slotted opening so that when the predetermined force is exerted on the cap to move the capsule from the pre-deployed to the deployed configuration, one of the pin and the middle portion deform to permit the pin to be slid proximally along the slotted opening.

In an embodiment, at least one of the clip arms may include an engaging feature configured to engage a portion of the cap so that, when a predetermined proximal force is exerted thereon, the capsule is moved from the pre-deployed configuration to the deployed configuration.

The present disclosure also relates to device for treating a target tissue, comprising a clip including a capsule extending longitudinally from a proximal end to a distal end and including a channel extending therethrough. Proximal ends of a pair of clip arms are slidably received within the channel so that the pair of clip arms are movable between an open configuration, in which distal ends thereof are separated from one another, and a closed configuration, in which the distal ends thereof are moved toward one another. The capsule further includes a cap mounted over a distal end of a longitudinal body so that, when a predetermined force is exerted on the cap via engaging features of the clip arms, the cap is moved from a pre-deployed configuration to the deployed configuration, in which the cap is moved proximally relative to the longitudinal body to reduce a length of the capsule. A proximal portion of the device is configured to permit insertion of the clip through a working channel of an endoscope. The proximal portion includes a flexible shaft extending from a proximal end to a distal end configured to be releasably coupled to the proximal end of the capsule. A control member extends through the flexible shaft to a distal end releasably coupled to proximal ends of the clip arms so that moving the control member longitudinally relative to the flexible shaft moves the clip arms between the open and the closed configurations.

In an embodiment, a distal end of the cap may include a shoulder for abutting the distal end of the longitudinal body to prevent further proximal movement of the cap relative to the longitudinal body.

In an embodiment, the clip arms may be biased toward the open configuration so that the clip arms are constrained toward the closed configuration via an interior surface of one of the cap and the longitudinal body.

In an embodiment, the cap may be coupled to the longitudinal body via a shear pin configured to fail when the predetermined force is exerted thereon.

In an embodiment, the cap may be coupled to the longitudinal body via a pin extending from an interior surface thereof and through a slotted opening extending through a wall along a distal portion of the longitudinal body, the pin longitudinally slidable from a distal end of the slotted opening, in the pre-deployed configuration, to a proximal end of the slotted opening, in the deployed configuration.

In an embodiment, the distal end of the slotted opening may be sized and shaped to correspond to a size and shape of the pin, the distal and proximal ends of the slotted opening connected via a middle portion having a width smaller than the distal end of the slotted opening so that when the predetermined force is exerted on the cap to move the capsule from the pre-deployed to the deployed configuration, one of the pin and the middle portion deform to permit the pin to be slid proximally along the slotted opening.

The present disclosure also relates to a method for treating a target tissue, comprising inserting a clip device through a working channel of an endoscope to a target site within a body until the clip device extends distally past a distal end of the working channel. The clip device includes a capsule and a pair of clip arms slidably received therein. The capsule further includes a cap mounted over a distal end of a longitudinal body. The clip device is moved between an open configuration, in which distal ends of the clip arms are separated from one another, and a closed configuration, in which the distal ends of the clip arms are drawn toward one another, until a target tissue is received between the distal ends as desired. The clip arms are drawn proximally into the capsule to move the clip toward the closed configuration to grip the target tissue between the clip arms. The clip is moved from a pre-deployed configuration toward a deployed configuration which reduces a length of the capsule by moving the clip arms further proximally relative to the so that an engaging feature of the clip arms engages the cap and exerts a predetermined proximal force thereon to move the cap proximally relative to the longitudinal body.

DETAILED DESCRIPTION

Figure 1:
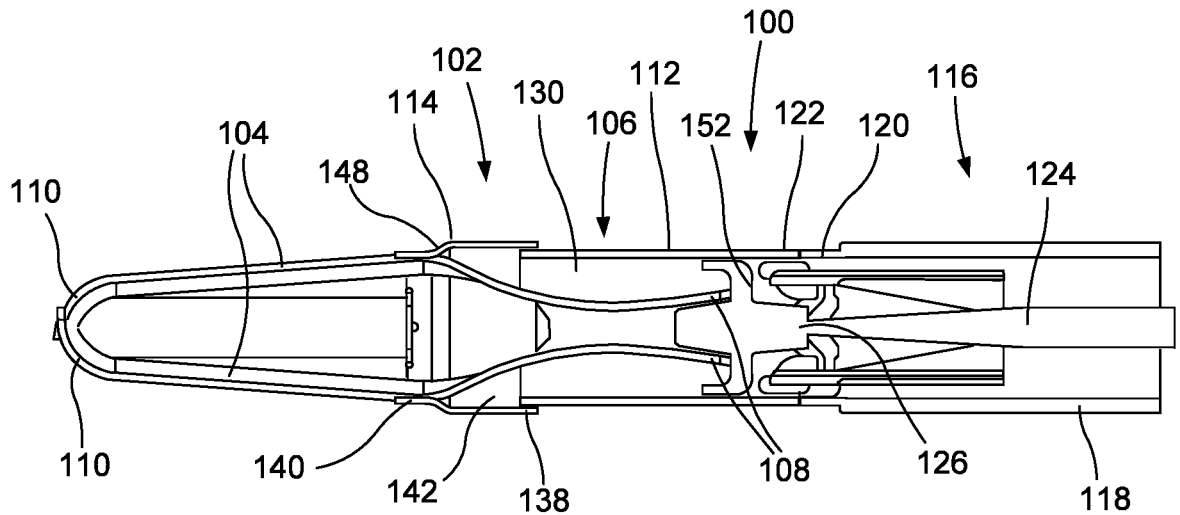
FIG. 1 shows a longitudinal cross-sectional view of the device of FIG. 1, in the pre-deployed configuration.
Figure 2:
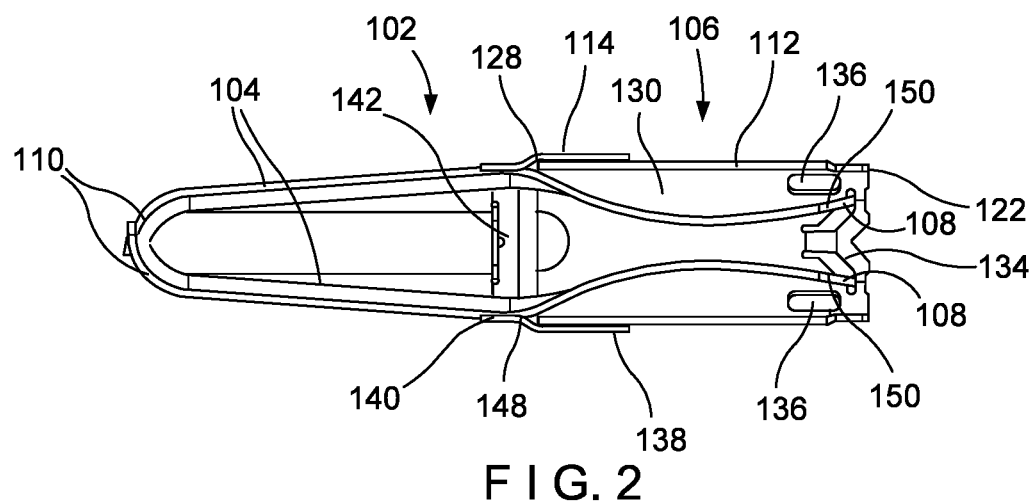
FIG. 2 shows a longitudinal cross-sectional view of the device of FIG. 1, in a deployed configuration.

The present disclosure may be further understood with reference to the following description and the appended drawings, wherein like elements are referred to with the same reference numerals. The present disclosure is directed to an endoscopic clipping device for treating tissue perforations, defects and/or bleeds. In some cases, a shorter deployed clip may be preferred to improve visualization of the target site and to allow better maneuverability when placing multiple clips. Exemplary embodiments of the present disclosure describe a clip comprising clip arms, proximal ends of which are slidably received within a capsule to move the clip between an open configuration and a closed configuration to clip a target tissue, as desired. As the clip is deployed over the target tissue in the closed configuration, the capsule collapses to reduce a length of the deployed clip, improving visibility of a target site and maneuverability when placing multiple clips. It should be noted that the terms proximal and distal, as used herein, are intended to refer to a direction toward (proximal) and away from (distal) a user of the device.

As shown in FIGS. 1-7, a clipping device 100 for treating tissue defects comprises a clip 102 including a pair of clip arms 104, proximal ends 108 of which are slidably received within a capsule 106 so that the clip 102 may move between an open configuration, in which distal ends 110 of the clip arms 102 are separated from one another, and a closed configuration, in which the distal ends 110 are drawn toward one another. The capsule 106 further comprises a longitudinal body 112 and a cap 114 coupled to one another and movable relative to one another from a pre-deployed configuration to a deployed configuration. In one embodiment, the cap 114 may be coupled to the longitudinal body 112 via, for example, a shear pin 132, which breaks or separates to move the capsule from the pre-deployed to the deployed configuration. As the capsule 106 is moved from the pre-deployed to the deployed configuration, the cap 114 moves relative to the longitudinal body 112 to reduce a length of the capsule 106 upon deployment. The device 100 is releasably coupled to a proximal portion 116 facilitating insertion of the device 100 to a target site, connecting the clip 102 to actuators accessible to a user (i.e., outside the body) to permit the user to control movement of the device 100 between the open and closed configurations and to deploy the device clip 102 over target tissue. The proximal portion 116 may include, for example, a flexible shaft 118 extending from a proximal end connected to a handle member (not shown) that remains outside the body, the handle including controls for moving and deploying the device 100 to a distal end 120 releasably coupled to a proximal end 122 of the capsule 106. The proximal portion 116 also includes a control member 124 extending from a proximal end connected to the controls of the handle member to a distal end 126 connected to the proximal ends 108 of the clip arms 102.

As described above, the capsule 106 includes the longitudinal body 112 and the cap 114. The longitudinal body 112 extends from the proximal end 122 to a distal end 128 and includes a channel 130 extending therethrough. In one embodiment, the proximal end 122 is configured to be releasably coupled to the distal end 120 of the flexible shaft 118. For example, the proximal end 122 may include tabs 134 that are crimped radially inward to engage a corresponding portion of a bushing at the distal end 120 of the flexible shaft 118. The longitudinal body 112 may also include locking windows 136 extending laterally through a wall thereof or other structures for engaging locking tabs 150 of the clip arms 104, as will be described in further detail below.

In one embodiment, the cap 114 is mounted over the distal end 128 so that the cap 114 is movable relative to the longitudinal body 112 from the pre-deployed to the deployed configuration. The cap 114 also extends longitudinally from a proximal end 138 to a distal end 140 with a channel 142 extending longitudinally therethrough so that channels 142, 130 of the cap 114 and the longitudinal body 112 are aligned to permit the clip arms 104 to slide longitudinally therein. In the pre-deployed configuration, the cap 114 is in a distal-most position relative to the longitudinal body 112. As the capsule 106 is moved from the pre-deployed to the deployed configuration, the cap 114 moves proximally relative to the longitudinal body 112 so that a length of the capsule 106 in the deployed configuration is shorter than a length of the capsule 106 in the pre-deployed configuration. In one embodiment, the distal end 140 of the cap 114 includes a shoulder 148 configured to engage the distal end 128 of the longitudinal body 112 to prevent the distal end 128 of the longitudinal body 112 from moving distally therepast. In other words, when the shoulder 148 engages the distal end 128 of the longitudinal body 112, the cap 114 is in a proximal-most position relative to the longitudinal body 112 and defines a minimum length of the capsule 106.

Figure 6:
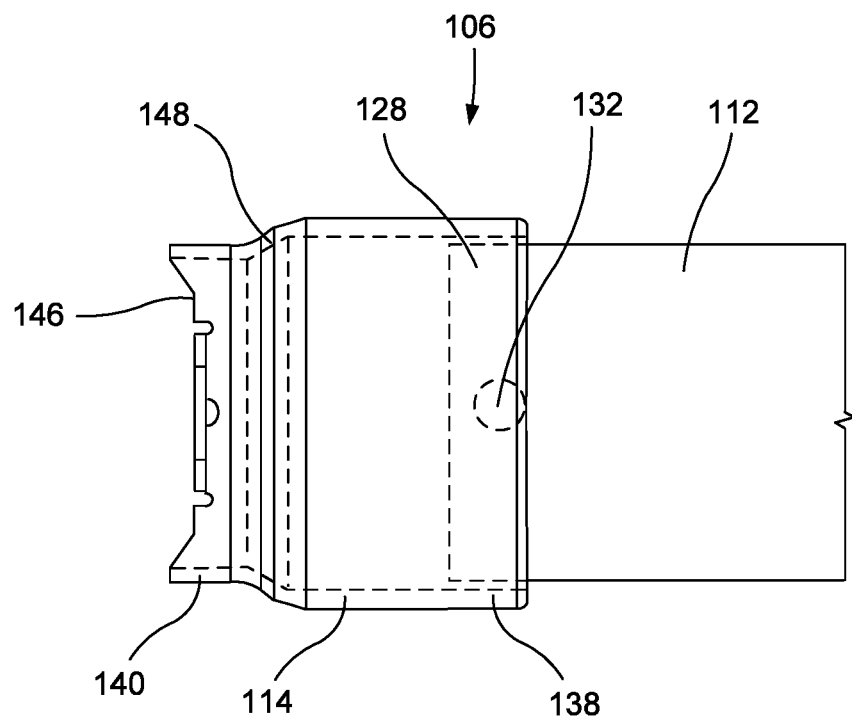
FIG. 6 shows an enlarged partially transparent view of a portion of the capsule of the device of FIG. 1, in the pre-deployed configuration.
Figure 7:
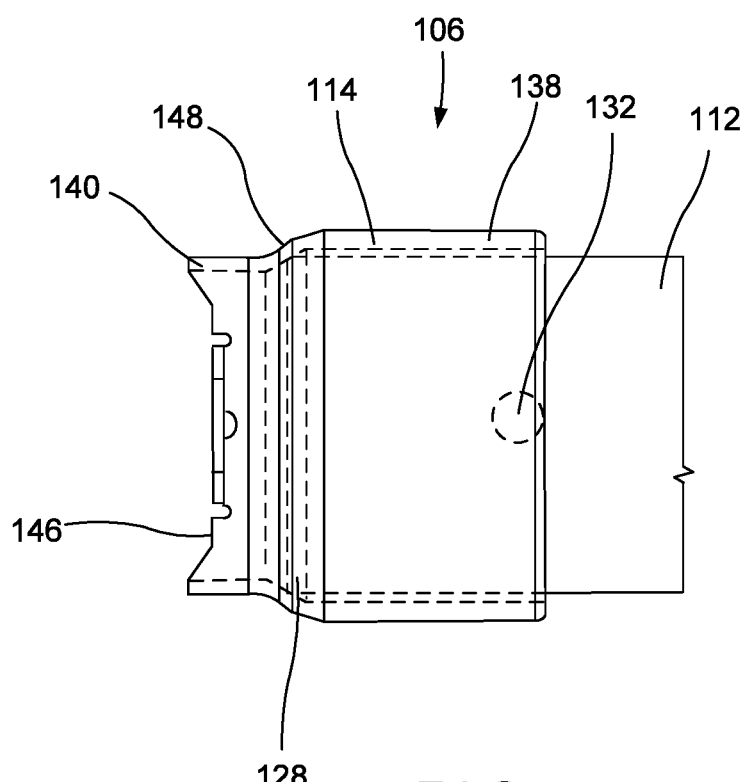
FIG. 7 shows an enlarged partially transparent view of the capsule of the device of FIG. 1, in the deployed configuration.

The cap 114 may be coupled to the distal end 128 of the longitudinal body 112 in any of a variety of ways. In one embodiment, the cap 114 may be overmolded to the longitudinal body 112. In one example, as shown in FIGS. 6-7, the cap 114 is overmolded to the distal end 128 of the longitudinal body 112 via a shear pin 132, in the pre-deployed configuration. The shear pin 132 is configured to break and/or separate when a predetermined force is exerted thereon. In one embodiment, when the clip arms 104 are drawn proximally relative to the capsule 106 to lock and deploy the clip 102, as will be described in further detail below, a portion of the one or both clip arms 104 engages the distal end 140 of the cap 114 so that a proximal force is exerted thereon. The proximal force exerted on the cap 114 breaks the shear pin 132 so that the cap 114 is freed to move proximally with respect to the longitudinal body 112, from the pre-deployed to the deployed configuration.

Each of the clip arms 104 extends from the proximal end 108 to the distal end 110. As described above, proximal portions of the clip arms 104 are slidably received within the channels 130, 142 of the longitudinal body 112 and the cap 114 of the capsule 106. In some embodiments, the proximal ends 108 of the clip arms 104 are slidably received within the longitudinal body 112 to move the clip 102 between the open and closed configurations. For example, as described above, the proximal ends 108 of the clip arms 104 may be coupled to the control member 124 (directly or indirectly) so that the clip arms 104 may be moved between the open and closed configurations via manipulation of the control member 124. In one embodiment, the clip arms 104 are biased toward the open configuration so that, in the closed configuration, the clip arms 104 are constrained toward one another via an interior surface of the cap 114 and/or the longitudinal body 112. When the clip arms 104 are moved distally to extend further out of the capsule 106, the clip arms 114 revert to their biased open configuration.

Figure 3:
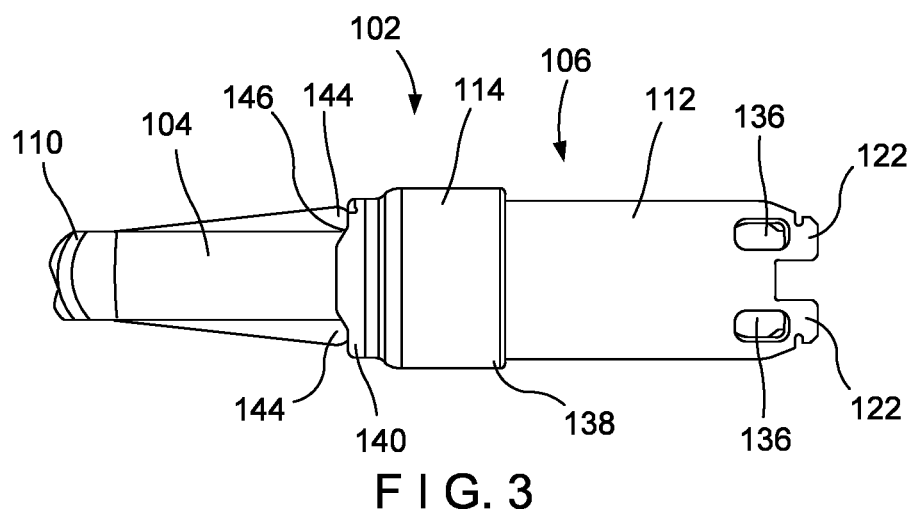
FIG. 3 shows a longitudinal side view of a device according to an exemplary embodiment of the present disclosure.
Figure 4:
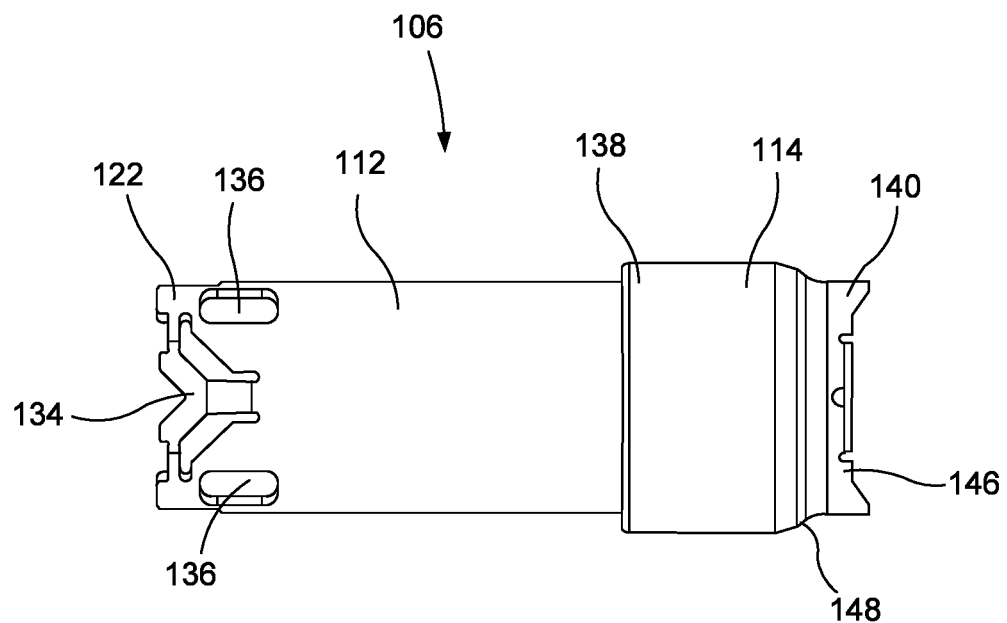
FIG. 4 shows a longitudinal side view of a capsule of the device of FIG. 1, in the pre-deployed configuration.
Figure 5:
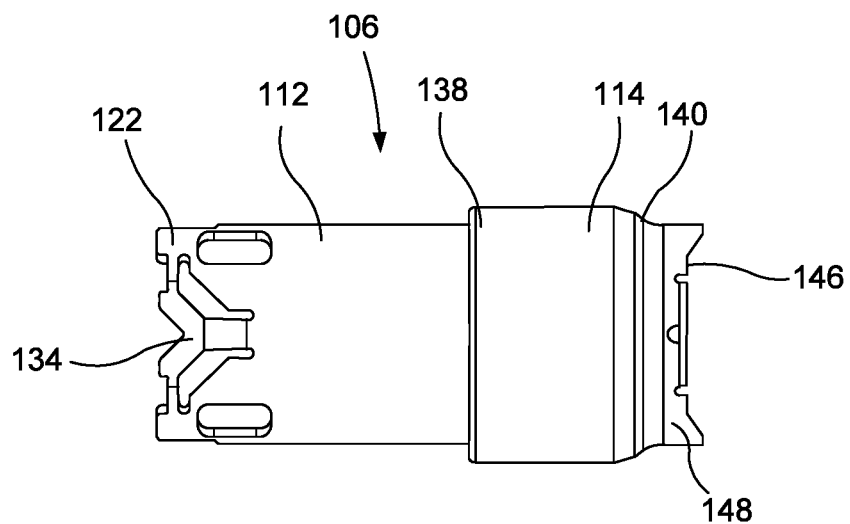
FIG. 5 shows a longitudinal side view of the capsule of the device of FIG. 1, in the deployed configuration.

Each of the clip arms 104 also includes an engaging feature 144 configured to engage a portion of the cap 114 to exert a proximal force thereon when the clip arms 104 are drawn proximally with respect to the capsule 106. In one embodiment, as shown in FIG. 3, the engaging features 144 extend from a portion of the clip arms 104 so that, when the clip arms 104 are drawn proximally relative to the capsule 106, the engaging features 144 abut a portion of a distal face 146 of the cap 114. The engaging features 144 are positioned along the clip arms 104 so that, when the engaging features 144 engage the cap 114, the clip arms 104 are drawn toward the closed configuration. In one example, the engaging features 144 are configured as wings extending from longitudinal edges of the clip arms 104.

Proximal ends 108 of the clip arms 104 also include locking tabs 150 extending therefrom. The proximal ends 108 in this embodiment are biased outward, away from a centerline of the capsule 106, but are restrained via the distal end 126 of the control member 124 until the clip 102 is being deployed. As will be described in further detail below, when it is desired to lock the clip 102 in the closed configuration, the clip arms 104 are moved proximally relative to the capsule 106 until the proximal ends 108 of the clip arms 104 are released from the control member 124 and the locking tabs 150 are permitted to spring outward and engage the locking windows 136 of the longitudinal body 112.

According to an exemplary method utilizing the device 100, the clip 102 is inserted through, for example, a working channel of an endoscope to a target site within a body while the handle member remains exterior to the body. The clip 102 is inserted through the working channel in the closed configuration. Once the clip 102 has reached the target site, the clip arms 104 are extended distally out of the capsule 106 and move under their natural bias toward the open configuration so that target tissue may be received between the clip arms 104. The clip 102 may be moved between the open and closed configurations by extending the control member 124 distally or withdrawing it proximally until a desired portion of target tissue is positioned between the clip arms 104, as desired. At this point, the clip 102 is drawn into the closed configuration to grip this portion of target tissue between the distal ends 110 of the clip arms 104 as desired. The clip 102 may be moved toward the locked configuration by, for example, drawing the control member 124 further proximally relative to the capsule 106 until the engaging features 144 engage the cap 114, as described above, exerting a proximal force on the cap 114 to break, separate or otherwise cause the shear pin 132 to fail. Upon breaking/separating of the shear pin 132, the cap 114 moves proximally relative to the longitudinal body 112 from the pre-deployed configuration to the deployed configuration, collapsing the capsule 106 and reducing a length of the capsule 106.

When the shoulder 148 of the cap 114 contacts the distal end 128 of the longitudinal body 112 and prevents the cap 114 from moving further proximally relative to the longitudinal body 112, the clip 102 is locked and deployed. According to one example, when the shoulder 148 engages the longitudinal body 112, the proximal force on the control member 124 causes the control member 124 to release from the proximal ends 108 of the clip arms 104, allowing the proximal ends 108 to revert to their biased configuration so that the locking tabs 150 engage the locking windows 136, thereby locking the clip 102 in the collapsed, closed configuration. The control member 124 is drawn proximally until an enlarged portion 152 at the distal end 126 of the control member 124 is positioned within the proximal end 122 of the longitudinal body 112 of the capsule 106 to move the inwardly crimped tabs 134 outward (i.e., away from a centerline of the capsule 106), out of engagement with, for example, the bushing at the distal end 120 of the flexible shaft 118. Further proximal motion of the control member 124 separates the control member 124 from the clip 102, freeing the clip 102 from the proximal portion of the device 100 and freeing it to remain in the body as the rest of the device 100 is removed from the body.

Although the exemplary embodiments show and describe a specific deployment mechanism, it will be understood by those of skill in the art that the clip 102 may be deployed via any of a number of deployment mechanisms so long as the capsule 106 collapses to reduce a length thereof during the deployment process. Specifically, as described above, the capsule 106 is collapsed via the proximal motion of the cap 114 relative to the longitudinal body. Although the exemplary embodiment describes and shows mounting of the cap 114 over the distal end 128 of the longitudinal body 112 in the pre-deployed configuration via a shear pin 132, it will be understood by those of skill in the art that the cap 114 may be temporarily fixed relative to the longitudinal body 112 in the pre-deployed configuration and moved toward the deployed configuration via any of a number of mechanisms.

Figure 8:
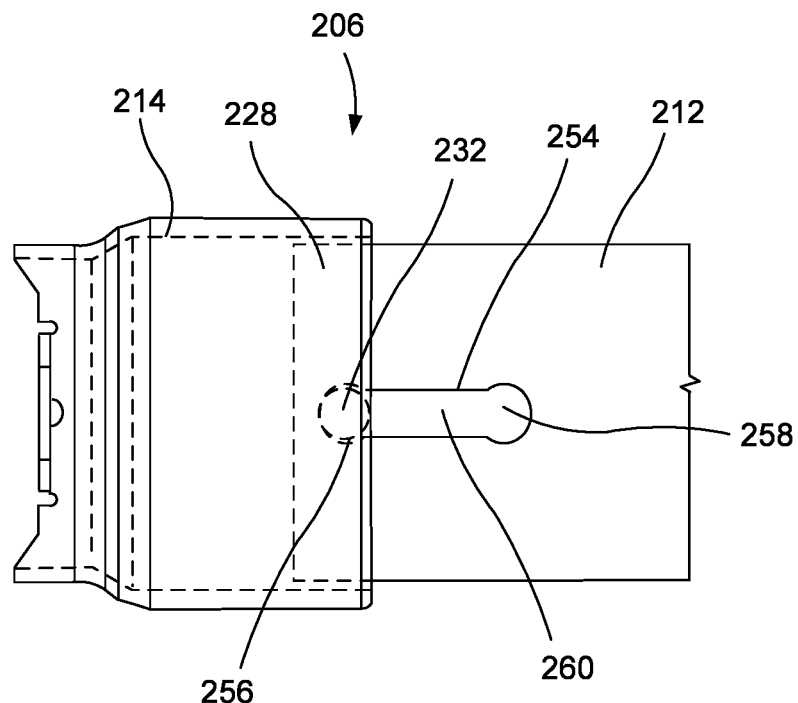
FIG. 8 shows an enlarged partially transparent view of a portion of a capsule of a device according to an alternate embodiment of the present disclosure, in a pre-deployed configuration.
Figure 9:
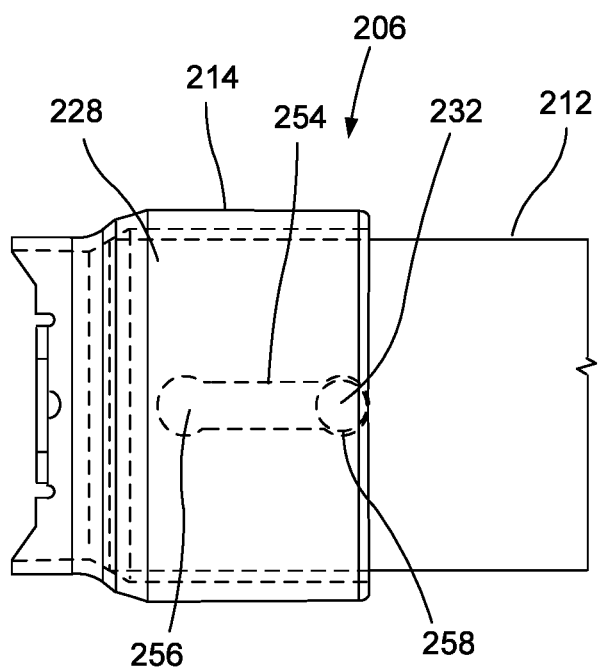
FIG. 9 shows an enlarged partially transparent view of a portion of the capsule of FIG. 8, in a deployed configuration.

For example, as shown in FIGS. 8-9, a capsule 206 may be substantially similar to the capsule 106 described above, and may be utilized in place of the capsule 106 in the device 100. Similarly to the capsule 106, the capsule 206 includes a cap 214 mounted over a distal end 228 of a longitudinal body 212 and movable relative thereto from a pre-deployed configuration to a deployed configuration. The cap 214 and the longitudinal body 212 may be substantially similar to the cap 114 and longitudinal body 112 described above with respect to the capsule 106. Rather than being mounted over the longitudinal body in the pre-deployed configuration via a shear pin, however, the cap 214 is coupled to the longitudinal body 212 via a pin 232 and slot 254.

In one embodiment, a distal portion of the longitudinal body 112 includes the slot 254 extending longitudinally through a wall thereof. The pin 232 extends from an interior surface of the cap 214 and through the slot 254 to couple the cap 214 to the longitudinal body 112. In a pre-deployed configuration, the pin 232 extends through a distal portion 256 of the slot 254 while in the deployed configuration, the pin 232 extends through the proximal portion 258 of the slot 254. The distal and proximal portions 256, 258 of the slot 254 are sized and shaped to correspond to a size and shape of the pin 232 received therein. A middle portion 260 of the slot 254 connecting the distal and proximal portions 256, 258 has a width smaller than a width of each of the distal and proximal portions 256, 258. In other words, where the pin 232 is cylindrical, a width of the middle portion 260 is smaller than a diameter of the pin 232 so that, to be moved from the pre-deployed to the deployed configuration, a predetermined force must be exerted on the pin 232, causing one of the pin 232 and/or the middle portion 260 to elastically deform allowing the pin 232 to slide along the middle portion 260 from the distal portion 256 to the proximal portion 258.

The capsule 206 may be utilized in substantially the same manner as the capsule 106. For example, as described above, in the pre-deployed configuration, the pin 232 is in the distal portion 256 of the slot 254 so that the cap 214 is in a distal-most position relative to the longitudinal body 212. Once the clip 102 has gripped a target tissue as desired, however, the clip arms 104 are drawn farther proximally relative to the capsule 206 until the engaging features 144 of the clip arms 104 engage the cap 214, exerting a proximal force on the cap 214 which deforms the pin 232 or the middle portion 260 of the slot 254 permitting the pin 232 to slide from the distal portion 256, through the middle portion 260 and to the proximal portion 254. When the pin 232 is received within the proximal portion 254, the cap 214 is in the proximal-most position relative to the longitudinal body 212, in the collapsed configuration. As described above, the clip 102 may then be locked and deployed, in the collapsed and closed configuration, as will be understood by those of skill in the art.

It will be apparent to those skilled in the art that various modifications may be made in the present disclosure, without departing from the scope of the disclosure.

What is claimed is:

1. A device for treating a target tissue, comprising:
   a clip including a capsule extending longitudinally from a proximal end to a distal end and including a channel extending therethrough, proximal ends of a pair of clip arms slidably received within the channel so that the pair of clip arms are movable between an open configuration, in which distal ends thereof are separated from one another, and a closed configuration, in which the distal ends thereof are moved toward one another, the capsule further including a cap coupled to a distal end of a longitudinal body so that, when a predetermined force is exerted on the cap via engaging features of the clip arms, the cap is moved from a pre-deployed configuration to the deployed configuration, in which the cap is moved proximally relative to the longitudinal body to reduce a length of the capsule; and
   a proximal portion configured to permit insertion of the clip through a working channel of an endoscope, the proximal portion including a flexible shaft extending from a proximal end to a distal end configured to be releasably coupled to the proximal end of the capsule and a control member extending through the flexible shaft to a distal end releasably coupled to the proximal ends of the clip arms so that moving the control member longitudinally relative to the flexible shaft moves the clip arms between the open and closed configurations.

2. The device of claim 1, wherein a distal end of the cap includes a shoulder for abutting the distal end of the longitudinal body to prevent further proximal movement of the cap relative to the longitudinal body.

3. The device of claim 2, wherein the shoulder engages the distal end of the longitudinal body, and the cap in the proximal-most position relative to the longitudinal body defines a minimum length of the capsule.

4. The device of claim 1, wherein the clip arms are biased toward the open configuration so that the clip arms are constrained toward the closed configuration via an interior surface of one of the cap and the longitudinal body.

5. The device of claim 1, wherein the cap is coupled to the longitudinal body via a shear pin configured to fail when the predetermined force is exerted thereon.

6. The device of claim 1, wherein the cap is coupled to the longitudinal body via a pin extending from an interior surface thereof and through a slotted opening extending through a wall along a distal portion of the longitudinal body, the pin longitudinally slidable from a distal end of the slotted opening, in the pre-deployed configuration, to a proximal end of the slotted opening, in the deployed configuration.

7. The device of claim 6, wherein the distal end of the slotted opening is sized and shaped to correspond to a size and shape of the pin, the distal and proximal ends of the slotted opening connected via a middle portion having a width smaller than the distal end of the slotted opening so that when the predetermined force is exerted on the cap to move the capsule from the pre-deployed configuration to the deployed configuration, one of the pin and the middle portion deform to permit the pin to be slid proximally along the slotted opening.

8. The device of claim 7, wherein the pin is cylindrical and the width of the middle portion is smaller than a diameter of the pin.

9. The device of claim 1, wherein a proximal portion of the longitudinal body includes locking windows extending through a wall thereof.

10. The device of claim 9, wherein the proximal ends of the clip arms include locking tabs which are configured to engage the locking windows of the longitudinal body when the capsule is in the deployed configuration.

11. The device of claim 1, wherein at least one of the clip arms includes an engaging feature configured to engage a portion of the cap so that, when a predetermined proximal force is exerted thereon, the capsule is moved from the pre-deployed configuration to the deployed configuration.

12. The device of claim 1, wherein the flexible shaft comprises a bushing and a proximal end of the longitudinal body comprises tabs configured to be crimped radially inward to engage a portion of the bushing to releasably couple the distal end of the flexible shaft to the longitudinal body.

13. A device for treating a target tissue, comprising:
a clip including a capsule extending longitudinally from a proximal end to a distal end with proximal ends of a pair of clip arms slidably received within the capsule so that the clip arms are movable between an open configuration in which distal ends thereof are separated from one another, and a closed configuration, in which the distal ends thereof are moved toward one another, the capsule including a cap slidably coupled to a distal end of a longitudinal body so that, when a predetermined force is exerted on the cap via an engaging feature on at least one of the clip arms, the cap is moved proximally relative to the longitudinal body to reduce a length of the capsule; and
a proximal portion configured to permit insertion of the clip through a working channel of an endoscope, the proximal portion including a flexible shaft extending from a proximal end to a distal end configured to be releasably coupled to the proximal end of the capsule and a control member extending through the flexible shaft to a distal end releasably coupled to proximal ends of the clip arms so that moving the control member longitudinally relative to the flexible shaft moves the clip arms between the open and closed configurations.

14. The device of claim 13, wherein a distal end of the cap includes a shoulder for abutting the distal end of the longitudinal body to define a maximum proximal movement of the cap relative to the longitudinal body.

15. The device of claim 14, wherein the shoulder engages the distal end of the longitudinal body when the cap has moved to a proximal-most position relative to the longitudinal body, and wherein the cap in the proximal-most position defines a minimum length of the capsule.

16. The device of claim 13, wherein the clip arms are biased toward the open configuration so that the clip arms are constrained toward the closed configuration via an interior surface of one of the cap and the longitudinal body as the clip arms are drawn into the capsule.

* * * * *